(12) United States Patent
Remond et al.

(10) Patent No.: US 10,351,263 B2
(45) Date of Patent: Jul. 16, 2019

(54) METHOD AND DEVICE FOR REMOTELY INSPECTING THE STATE OF AN AIRCRAFT ENGINE

(71) Applicant: Safran Aircraft Engines, Paris (FR)

(72) Inventors: Florie Remond, Yerres (FR); Erwan Guerin, Lieusaint (FR); Jade Guyenne, Cognac (FR); Bernard Lhermenier, Ris Orangis (FR); Sylvain Squedin, Bondoufle (FR)

(73) Assignee: SAFRAN AIRCRAFT ENGINES, Paris (FR)

( * ) Notice: Subject to any disclaimer, the term of this patent is extended or adjusted under 35 U.S.C. 154(b) by 79 days.

(21) Appl. No.: 15/552,634

(22) PCT Filed: Feb. 22, 2016

(86) PCT No.: PCT/FR2016/050401
§ 371 (c)(1),
(2) Date: Aug. 22, 2017

(87) PCT Pub. No.: WO2016/135402
PCT Pub. Date: Sep. 1, 2016

(65) Prior Publication Data
US 2018/0346150 A1    Dec. 6, 2018

(30) Foreign Application Priority Data
Feb. 23, 2015 (FR) ...................... 15 51523

(51) Int. Cl.
*B64F 5/60* (2017.01)
*G01M 11/08* (2006.01)
(Continued)

(52) U.S. Cl.
CPC ............. *B64F 5/60* (2017.01); *G01M 11/081* (2013.01); *G01M 15/14* (2013.01);
(Continued)

(58) Field of Classification Search
CPC ....... B64F 5/60; G01M 11/081; G01M 15/14; G01N 21/8851; G02B 23/24
See application file for complete search history.

(56) References Cited

U.S. PATENT DOCUMENTS

| 6,850,252 B1 * | 2/2005 | Hoffberg | G06K 9/00369 348/E7.061 |
| 2005/0222933 A1 * | 10/2005 | Wesby | G06Q 40/00 705/36 R |

(Continued)

FOREIGN PATENT DOCUMENTS

| EP | 0 725 373 A2 | 8/1996 |
| JP | 2004-024340 A | 1/2004 |
| WO | 01/71500 A1 | 9/2001 |

OTHER PUBLICATIONS

Search Report issued in French Patent Application No. 1551523 dated Jan. 14, 2016.
(Continued)

*Primary Examiner* — Mishawn N. Hunter
(74) *Attorney, Agent, or Firm* — Pearne & Gordon LLP

(57) ABSTRACT

The invention relates to an assistance device for remote diagnostics during verification of the state of an aircraft engine, carried out in situ by at least one operator with an endoscope used to capture images of the engine and to take measurements intended to be transmitted to at least one remote terminal used by at least one remote expert, with the aim of performing a collaborative analysis of the images and the measurements. The device according to the invention further comprises a portable housing controlled by the operator and equipped with a software module intended for generating an operational context as a function of location data provided by a GPS, weather data from the endoscopy location, and data on the communications network.

13 Claims, 2 Drawing Sheets

(51) Int. Cl.
*G01M 15/14* (2006.01)
*G02B 23/24* (2006.01)
*G01N 21/88* (2006.01)
*G06T 7/00* (2017.01)
*G07C 5/00* (2006.01)
*H04N 7/08* (2006.01)
*H04N 7/18* (2006.01)

(52) U.S. Cl.
CPC ......... *G01N 21/8851* (2013.01); *G02B 23/24* (2013.01); *G06T 7/0004* (2013.01); *G07C 5/008* (2013.01); *H04N 7/08* (2013.01); *H04N 7/185* (2013.01)

(56) References Cited

U.S. PATENT DOCUMENTS

| | | | |
|---|---|---|---|
| 2008/0109187 A1 | 5/2008 | Kollgaard | |
| 2009/0152391 A1* | 6/2009 | McWhirk | B64B 1/02 244/30 |
| 2010/0246605 A1* | 9/2010 | Taylor | H04N 7/163 370/477 |
| 2013/0114878 A1* | 5/2013 | Scheid | G06T 7/001 382/141 |
| 2013/0332004 A1* | 12/2013 | Gompert | G07C 5/008 701/1 |
| 2014/0111647 A1* | 4/2014 | Atsmon | H04N 7/185 348/148 |
| 2014/0198211 A1* | 7/2014 | Giuffrida | H04N 7/185 348/144 |
| 2014/0208163 A1 | 7/2014 | Domke | |
| 2015/0019266 A1* | 1/2015 | Stempora | G06Q 40/08 705/4 |
| 2016/0077019 A1* | 3/2016 | Mathon | G01N 21/898 356/238.1 |
| 2017/0030840 A1 | 2/2017 | Bugeaud-Remond | |

OTHER PUBLICATIONS

International Search Report issued in Application No. PCT/FR2016/050401 dated May 30, 2016.

Written Opinion issued in Application No. PCT/FR2016/050401 dated May 30, 2016.

* cited by examiner

METHOD AND DEVICE FOR REMOTELY INSPECTING THE STATE OF AN AIRCRAFT ENGINE

TECHNICAL DOMAIN

The domain of the invention is checking of aircraft engines under development or in maintenance after a landing following a flight, or in programmed maintenance, and more specifically relates to a device and a method to provide assistance for a remote diagnostic during a check of the state of an aircraft engine made in situ by an operator using an endoscope or camera used to capture images of said engine and to make measurements that will be transmitted with documentation and reference images to at least one remote terminal used by at least one remote expert to make a collaborative analysis of said images and said measurements, the device also comprising a portable housing that can be connected to a monitor and provided with means of wireless communication with the endoscope and means of allowing the operator to manually and/or automatically enrich the captured images and the measurements made with audio and/or video and/or text comments.

The invention also relates to a method of providing aid for a remote diagnostic during an endoscopy of an aircraft engine.

The invention also relates to a computer program stored on a recording medium and containing instructions for performing steps in the method.

STATE OF PRIOR ART

During the verification of the state of an aircraft engine after a landing following a flight, during programmed maintenance or during tests during the development of a propulsion assembly or components of aircraft engines, engine parts are verified and tested in situ by operators at the root of the aircraft wing or in development, test or maintenance installations. These engines may sometimes be expertised by technical experts who are not always located on the site of the checks and the tests and who have to visit the site to see the state of components and to give their technical opinions and recommendations to operators. In particular, experts need to analyse defects observed during endoscopies and to do this, they need information that they can use to determine the nature of the defect or the damage. Therefore the expert needs to be able to communicate with the endoscopy operator to collect all data necessary for his analysis so that he can produce a reliable diagnostic and give relevant recommendations about actions to be taken to deal with this problem.

Furthermore, decisions must be made quickly and unambiguously to determine damage levels so that the aircraft can be returned to service quickly, or so that the test campaign can be completed.

At the present time, technical decisions involving several sites and remote persons are made after several telephone discussions or emails that can include photos or videos.

This procedure involves repeated iterations when there are misunderstandings between operators performing the tests and analysts analysing the results of these tests or expertises. This obliges operators to take very many photos to be sure that they do not miss a critical area of the engine being checked. Technical information in the aviation field must be shared unambiguously, for safety reasons. To achieve this, remote experts must have measurements, images and videos taken from specific viewing angles.

Consequently, operators working adjacent to the installation need to be able to move around easily to be able to access the different zones to be checked. This is not always possible with existing aircraft due to the space occupied by the use of several tools connected by several cables that hinders operators working on aircraft to be tested, and since both hands of operators are often necessary in the very confined space in which they are working under the wing (only a few centimeters of clearance).

Furthermore, if communication conditions are not optimal (presence of disturbances, lack of network coverage, electromagnetic disturbances), the quality of the images and the measurements made may not be good enough for experts to be able to make a reliable diagnostic.

One purpose of the invention is to enable operators making the measurements to have unhindered access to all zones of the engine to be checked and to be able to move around while making the inspection and measurements, and to share them with remote experts in real time.

Another purpose of the invention is to provide experts with precise information, and particularly measurements made and images taken in key zones so that they can make a diagnostic regardless of weather conditions and regardless of the topology of the location in which the tests are being made.

PRESENTATION OF THE INVENTION

This purpose is achieved through the use of a small and compact device adapted to all types of endoscopic equipment and analogue cameras, and to all contexts of endoscopies or videos of propulsion assemblies or components (underwing, removed, etc.), so that operators located on the inspection and test site can reach the different zones of the propulsion assembly under test without constraint, to quickly identify and display any defects and to communicate captured images and measurement results in real time.

This device comprises at least one endoscope provided with a camera used in situ by at least one operator to capture images of said engine and to make measurements to be transmitted to at least one remote terminal for use by at least one remote expert in readiness for a collaborative analysis of said images and said measurements.

The device according to the invention also comprises a portable housing controlled by the operator located on the inspection and test site provided with means of wireless communication with the endoscope and means by which said operator can manually or automatically enrich the captured images and measurements made with audio and/or video and/or test comments.

Said portable housing also comprises a software module to generate an operations context as a function of positioning data provided by a GPS, weather data at the location of the endoscopy and data on the communications network and descriptive data of progress of the endoscopy. Weather data include temperature, pressure and air humidity information characterising the atmospheric context of the endoscopy. Description data about progress with the endoscopy can be kept in a log of events for example generated automatically by the endoscope, or by the portable housing and mentioning anomalies in the endoscopy procedure such as an error from a measurement module.

Remote experts can refer to the added audio and/or video and/or text comments, to guide the operator located on the inspection and test site during the tests. Experts can help to make decisions and envisage corrective actions within very short times.

Said portable housing also comprises a wireless communication interface that operators located on the inspection and test site can use for exchanges with the expert of the captured images, documentation and the results of measurements made enriched with audio and/or video and/or text comments, in real time and interactively.

Thus, when remote experts receive the coordinates of the head of the endoscope at which a possible anomaly is found, after examination of the possible anomaly on images transmitted by the operator, they can send instructions to the operator to guide him in making measurements and/or taking images of other parts and at other positions on the engine.

In one preferred embodiment of the invention, the portable housing comprises an encoder to adjust the rate of information exchanged with the remote terminal as a function of network characteristics so as to maintain a maximum image quality and minimum latency. Note that the portable housing can be configured to transmit reduced information to the remote terminal in the case of disturbances on the communication network. Said reduced information includes the coordinates of the endoscope head, one image per second or only one relevant image representative of an anomaly and to send at least one image to the remote terminal following automatic detection of a particular pattern that could represent an anomaly.

The remote terminal comprises a virtual representation of said engine in three dimensions (3D) that remote experts can use to search for an anomaly in the engine, to locate an anomaly using the coordinates of the endoscope head, and a software fault search module configured to compare the image captured by the endoscope with at least one model or pattern of anomalies previously memorised in a first database.

Said virtual representation is a virtual three-dimensional (3D) mockup of said engine.

The remote terminal receives the coordinates of the endoscope head corresponding to a possible anomaly, these coordinates are used by the software fault search module that locates the position indicated on the 3D mockup. The remote expert can then examine the possible anomaly on the images transmitted by the operator and possibly send instructions to the operator to guide him in making other measurements and/or taking other images.

Note that the software fault search module can also be implemented in a remote server comprising a data base and statistical analysis models.

The housing also comprises connections to an audio helmet, a tablet and/or a laptop computer and a memory to save captured information and images and exchanged measurements, and a conversion module to convert captured images in a data format specific to the endoscope to a data format that can be used by the remote terminal.

The remote diagnostic assistance method according to the invention includes the following steps:
- transmitting said images and said measurements from the endoscope to a portable housing that can be connected to a monitor and monitored by the operator;
- manually and/or automatically enriching said images and said measurements with audio and/or video and/or text comments,
- exchanging images, measurements, documentation and reference images between said portable housing and said remote terminal used by the expert in real time and interactively through a wireless connection, to analyse said images and said measurements and to collaboratively create a diagnostic.

This method also comprises a preliminary step consisting of generating an operations context as a function of positioning data provided by a GPS, weather data at the location of the endoscopy and data on the communications network.

The method also comprises a connectivity test and a bandwidth calculation to check if the network has a reliable communication between the portable housing and the remote terminal, and a step consisting of adjusting the rate of information exchanged between the portable housing and the remote terminal as a function of the characteristics of the network so as to keep a maximum image quality and minimum latency.

In one variant embodiment, the method according to the invention also comprises a step consisting of transmitting reduced information to the remote terminal in case of disturbances on the communication network.

The method according to the invention is implemented using a computer program memorised on a recording medium and containing instructions for performing the steps in said method when it is run on a tablet or a computer.

BRIEF DESCRIPTION OF THE DRAWINGS

Other characteristics and advantages of the invention will become clear from the description given below used as a non-limitative example, with reference to the appended figures among which.

DETAILED PRESENTATION OF PARTICULAR EMBODIMENTS

Figure 1:
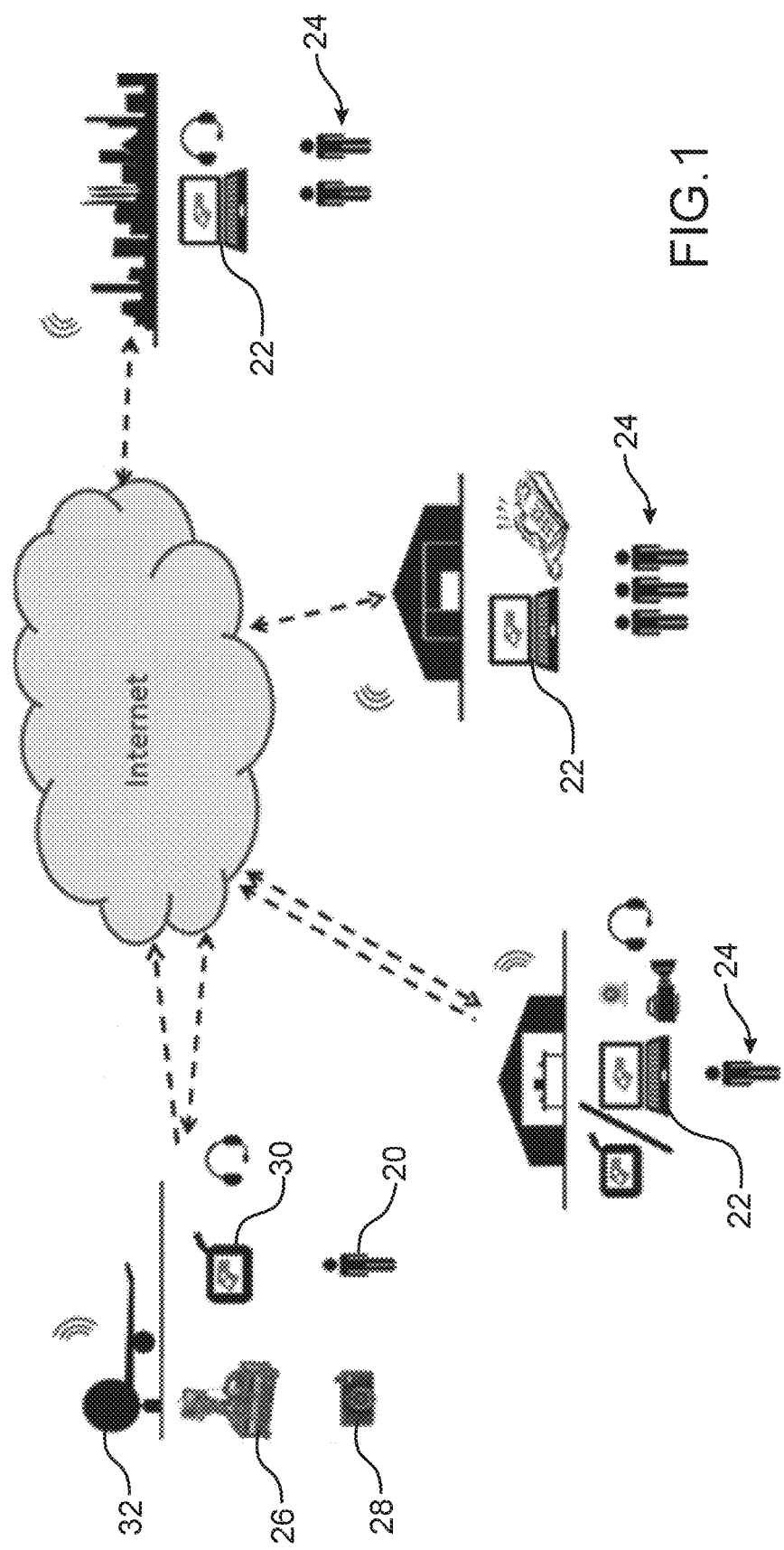
FIG. 1 diagrammatically shows a device according to the invention.

FIG. 1 diagrammatically shows a device for providing assistance with a remote diagnostic during the check on the state of an aircraft engine, for example an endoscopy, performed in situ by operators 20 in position at the root of the aircraft wing or in development, test or maintenance installations, to capture images particularly inside the aircraft engine and to capture measurements that will be transmitted to several remote terminals 22 used by several experts 24 in readiness for a collaborative analysis of said images and said measurements. The images and measurements are made using an endoscope 26 or a camera 28 communicating on a wireless link with a portable housing 30.

In one preferred embodiment, a tablet is physically associated with the portable housing to form a compact assembly.

In the remainder of this description, the portable housing 30 will designate this compact assembly.

In one alternative embodiment, the portable housing is independent of the tablet or the portable computer or any other man machine interface with which it communicates, for example through a wireless link.

In the preferred embodiment, the operations context of the endoscopy is generated by a software module integrated into the portable housing 30 as a function of positioning data supplied by a GPS, weather data at the location of the endoscopy and data on the communications network. Thus, at the beginning of publication of images and measurements and throughout the endoscopy, this software module extracts the context making use of several information sources:
- GPS or other positioning system;

Weather data related to the location of the endoscopy, for example using APIs (Application Programming Interface);

Timestamp information related to the publication of measurements made and captured images;

Data about the location of the endoscopy, airport data (eg altitude, etc.);

Network data: network type, throughout, jitter, latency, etc.

Information is recorded to be provided in a final report on the endoscopy.

Knowledge of the operations context makes it possible to determine ideal encoding parameters for the publication of images and measurements, at all times.

The housing 30 also comprises software that operators 20 can use to enrich captured images and measurements made with audio and/or video and/or text comments. These comments can be entered manually using a virtual keyboard or using a voice control and/or automatically using a NFC (Near Field Communication) reader or an inertial unit associated with the endoscope 26. These comments can contain information about progress with the endoscopy.

Furthermore, the housing 30 is equipped with a wireless communication interface that provides a connection to the Internet network through an antenna 32 positioned on the site of the installations. The housing 30 also comprises a connectivity test module and a bandwidth calculation model that will check if the network can carry reliable communication between the operators 20 and experts 24, and estimate the maximum possible bit rate between the housing 30 and the remote terminals 22.

In order to maintain maximum image quality and minimum latency, the housing 30 also includes an encoder that adjusts the data rate and information transmitted as a function of network characteristics and encoding parameters determined by an acquisition board integrated into the housing 30. Encoding parameters include for example the resolution (eg. 1024×768), the number of frames per second (eg. 24 fps) and the encoder type (eg. H264, VP8). The encoder uses these parameters to adjust encoding of video images as a function of the selected network. Thus, when the bandwidth of the network is too low to pass the video flow, the encoder can transmit reduced information such as the coordinates of the endoscope head, and one image per second or possibly one image selected by the operator, and the measurements made. The remote terminal on which the expert is working can comprise a three-dimensional virtual mockup of the engine. With positioning information about the part in the engine and the head of the endoscope, a view angle and an image, the expert can position and display the target part in the engine and thus ask the operator to take other photos to analyse a fault.

In another embodiment, an image can be sent to the expert following automatic detection of a particular pattern revealing damage.

The operator and remote experts interactively exchange captured images, the results of measurements made in the operational context of the endoscopy, documentation and reference images enriched by audio and/or video and/or text comments, and information about the position of the camera and measurement probes. Remote experts analyse received information and if necessary guide the operator in precisely pinpointing measurement points and photo positions.

Figure 2:
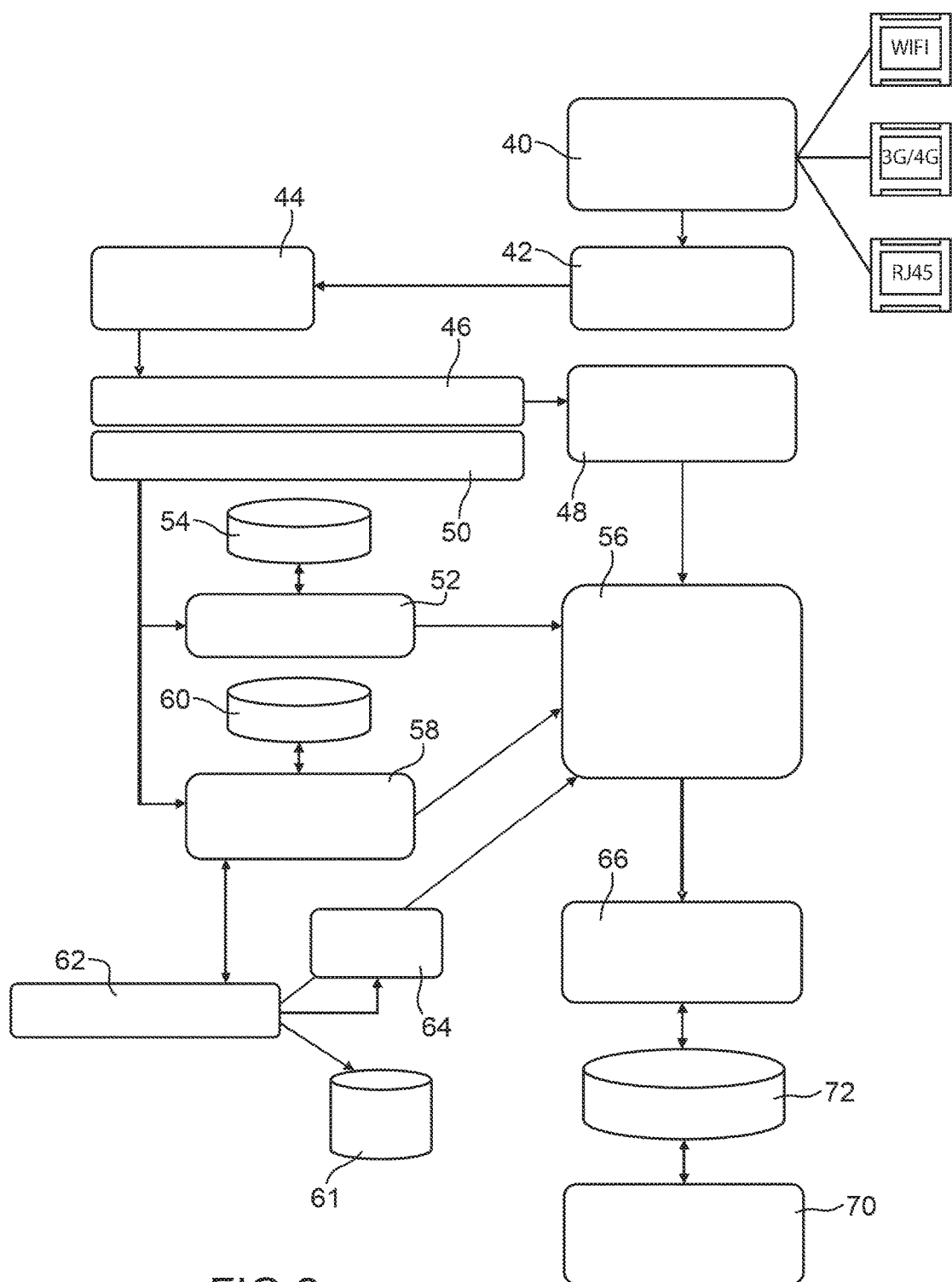
FIG. 2 diagrammatically shows the steps in a method according to the invention.

FIG. 2 illustrates the steps in a test and collaborative analysis session made using the device according to the invention.

Before making the endoscopy, in step 40, the operator 20 starts a connectivity and search test for available networks. During this step, the connectivity test module calculates the bandwidth and, in step 42, selects the most appropriate data rate to make reliable exchanges between the housing 30 and remote terminals 22.

In step 44, the operator 20 makes measurements and captures video images on zones of the engine to be tested.

In step 46, the encoder encapsulates video packets in a transport protocol (eg. RTP, RTMP) to publish the video flow through the internet network to a video or image and/or sound sharing server, to which the remote experts 24 can connect, for example through a WIFI link, to recover the published information. The experts can also receive this information directly on each of their terminals.

Note that the context generator extracts information describing the context of the endoscopy at the beginning of the publication of the measurements and the video flow, and throughout the endoscopy (step 48). This information is then recorded to be provided later in the final report on the endoscopy. Remote experts 24 use the context data to make a detailed analysis of phenomena detected during the endoscopy and to produce a precise diagnostic on the causes of damage.

The video capture system of the endoscope extracts one image out of twenty-four per second (step 50) (24 fps). This image is then processed by a fault search software module installed in the housing 30 and dedicated to either detection of anomalies or recognition of the QR code or any other engine parts marking system. The software fault search module saves a time history (timestamp) information related to the publication of the measurements made and captured images, in the memory of the housing 30. In one alternative embodiment, image processing may be done by a remote server.

In step 52, the software fault search module compares the extracted image or part of this image with models or patterns of anomalies previously memorised in a first database 54. This database can be recorded in a remote server accessible to remote experts 24. If an anomaly is detected or if a threshold of uncertainty is reached, the fault search software generates notifications that are displayed on the screen of the tablet associated with the housing 30 and on the screens of remote terminals 22. The operator 20 enriches these notifications of audio and/or video comments transmitted in real time (step 56) to the remote experts 24. Other information is automatically added to the captured images from an NFC (Near Field Communication) reader and/or an inertial unit associated with the endoscope 26. Information collected by the NFC reader is data characterising the part of the engine on which an NFC chip is placed. For example, the NFC reader helps to identify a part and to find its position on the three-dimensional virtual mockup representative of the engine. Experts can make use of the position of the part on the virtual mockup to interactively guide the operator 20, by precisely indicating zones to be identified. Experts use other information such as the date on which the part was put into service, and its characteristics and source to perform their analysis of the endoscopy.

In step 58, the fault search module reads the QR code or any other visual marking system of the part, and refers to a second database 60 containing information about all engine parts and their locations and their corresponding functions in the propulsion assembly.

Preferably, the position of the part in the propulsion assembly makes use of three potential sources of information:

Inertial unit, onboard the endoscopic camera, that provides displacement information and uses information on engine drawings memorised in a third database 61 to estimate the position of the camera. This information is automatically added to the captured images.

The positioning information provided in step 58 from recognition of visual tags like a QR code;

The information obtained by reading an RFC tag (or similar) by means of a reader installed on the camera head.

In step 62, positioning data, detection/recognition data of parts or anomalies obtained during the previous steps are automatically added to the video flow in real time, for transmission to the experts 24. These data are then displayed in step 64.

Positioning data are used to texture the mockup in three dimensions with images transmitted by the video flow. The positioning data then have to be made to correspond to the three-dimensional mockup by making position calibrations if necessary. For example, if position information is biased, the three-dimensional mockup can possibly be used to correct it by making an interpolation of the current position of the endoscope head as a function of previous positions of the endoscope head and a projection of the current position on the three-dimensional mockup. In one alternative embodiment, calibration data can be transmitted to the inertial unit to correct its positioning data.

Advantageously, the association of the image flow and the three-dimensional mockup can be used to immerse the expert in the context of the endoscopy.

In step 66, data produced during the session are combined on a time line, to that the video can be replayed, or the documentation or reference images can be found with all endoscopic observation data.

If experts consider that they have received sufficient information in real time to create a diagnostic, they transmit their diagnostic to the operator 20 directly, either orally or through a messaging service. At the end of the inspection, the shared session is interrupted and data (video photo measurements, conversations, etc.) exchanged during the session are stored (step 70) in a memory 72.

The device according to the invention provides a hardware and software solution based on standard interfaces and can be adapted to all types of endoscopic equipment and cameras (and not to a single brand or a single model) and to all endoscopy and video contexts of propulsion assemblies or components.

What is claimed is:

1. Assistance device for a remote diagnostic during verification of the state of an aircraft engine, carried out in situ by at least one operator (20) by means of an endoscope (26) or a camera, used to capture images of said engine and measurements that will be transmitted to at least one remote terminal (22) used by at least one remote expert (24) to make a collaborative analysis of said images and said measurements, the device also comprising a portable housing (30) that can be connected to a monitor and monitored by the operator (20), said portable housing (30) being provided with means of wireless communication with the endoscope (26) and means of allowing the operator (20) to manually and/or automatically enrich the captured images and the measurements made with audio and/or video and/or text comments, said portable housing (30) comprising a software module to generate an operations context as a function of positioning data provided by a GPS, weather data at the location of the endoscopy and data on a communications network so as to determine ideal encoding parameters for publication of images and measurements so that the at least one remote expert may use the context data to make a detailed analysis of phenomena detected during the endoscopy and to produce a precise diagnostic on causes of damage, the device characterised in that the portable housing (30) is configurable to send at least one image to the remote terminal (22) following automatic detection of a particular pattern that could represent an anomaly.

2. Device according to claim 1, in which said portable housing (30) also comprises a wireless communication interface that the operator (20) can use for exchanges of captured images, results of measurements made, documentation and reference images enriched with audio and/or video and/or text comments, with remote experts (24), in real time and interactively, and a memory (72) to save captured information and images and the results of measurements exchanged between the operator (20) and the remote experts (24).

3. Device according to claim 1, in which said portable housing (30) also comprises a connectivity test module and a bandwidth calculation model that will check if the communications network can carry reliable communication with the remote terminal (22).

4. Device according to claim 3, in which said portable housing (30) also comprises an encoder to adjust the rate of information exchanged with the remote terminal (22) as a function of network characteristics so as to maintain a maximum image quality and minimum latency.

5. Device according to claim 4, in which said portable housing can also be configured to transmit reduced information to the remote terminal (22) in the case of disturbances on the communications network.

6. Device according to claim 5, in which said reduced information includes coordinates of an endoscope head, one image per second or only one relevant image representative of an anomaly.

7. Device according to claim 1, in which the remote terminal (22) comprises a virtual representation of the engine.

8. Device according to claim 7, in which said virtual representation is a virtual three-dimensional mockup of the engine.

9. Method for assistance with remote diagnostic during a verification of the state of an aircraft engine to make a collaborative analysis of images and measurements made by an operator (20) using an endoscope (26) or a camera and that will be sent to at least one remote expert (24), the method including the following steps:

transmitting said images and said measurements from the endoscope (26) to a portable housing (30) that can be connected to a monitor and checked by the operator (20);

manually and/or automatically enriching said images and said measurements with audio and/or video and/or text comments, exchanging images, measurements, documentation and reference images between said portable housing (30) and a remote terminal (22) used by the expert (24) in real time and interactively through a wireless connection, to analyse said images and said measurements and to collaboratively create a diagnostic, characterised in that it also comprises a preliminary step consisting of:

generating an operations context as a function of positioning data provided by a GPS, weather data at the location of the endoscopy and data on a communications network so as to determine ideal encoding parameters for publication of images and measurements so that the at least one remote expert may use the context data to make a detailed analysis of phenomena detected during the endoscopy and to produce a precise diagnostic on causes of damage, wherein said portable housing (30) sends at least one image to the remote terminal (22) following automatic detection of a particular pattern that could represent an anomaly.

10. Method according to claim 9 also comprising a connectivity test and a bandwidth calculation to check if the communications network has a reliable communication between the portable housing (30) and the remote terminal (22).

11. Method according to claim 10 also comprising a step to adjust the rate of information exchanged between the portable housing (30) and the remote terminal (22) as a function of network characteristics so as to maintain a maximum image quality and minimum latency.

12. Method according to claim 11 also comprising a step to transmit reduced information to the remote terminal (22) in the case of disturbances on the communications network.

13. Method according to claim 12, in which said reduced information includes coordinates of an endoscope head, one image per second or only one relevant image representative of an anomaly.

* * * * *